United States Patent
Onishi

(10) Patent No.: US 7,534,916 B2
(45) Date of Patent: May 19, 2009

(54) PROCESS FOR PRODUCING METHIONINE

(75) Inventor: Kozo Onishi, Niihama (JP)

(73) Assignee: Sumitomo Chemical Company, Limited, Tokyo (JP)

(*) Notice: Subject to any disclaimer, the term of this patent is extended or adjusted under 35 U.S.C. 154(b) by 0 days.

(21) Appl. No.: 11/785,942

(22) Filed: Apr. 23, 2007

(65) Prior Publication Data

US 2007/0246129 A1   Oct. 25, 2007

(30) Foreign Application Priority Data

Apr. 25, 2006 (JP) ............... P2006-120176
Dec. 11, 2006 (JP) ............... P2006-333069

(51) Int. Cl.
*C07C 323/03* (2006.01)

(52) U.S. Cl. .................................. 562/559

(58) Field of Classification Search ........ None
See application file for complete search history.

(56) References Cited

U.S. PATENT DOCUMENTS

2004/0267049 A1* 12/2004 Kawabe et al. ............. 562/557

FOREIGN PATENT DOCUMENTS

JP    11-217370    * 10/1999
JP    2003-104960   4/2003

* cited by examiner

*Primary Examiner*—Paul A Zucker
(74) *Attorney, Agent, or Firm*—Sughrue Mion, PLLC

(57) ABSTRACT

In the process for producing methionine of the present invention uses, as an equipment material for a step of hydrolyzing 5-(β-methylmercaptoethyl)hydantoin in the presence of potassium carbonate to produce methionine, a stainless steel containing 21.0 to 30.0% by weight of a Cr element, 2.5 to 11.0% by weight of a Ni element and 1.0 to 5.0% by weight of a Mo element, a ratio of the total content of the Cr element and the Mo element to the content of the Ni element being from 4.7 to 14.0, is used.

8 Claims, No Drawings

PROCESS FOR PRODUCING METHIONINE

BACKGROUND OF THE INVENTION

1. Technical Field

The present invention relates to a process for stably producing methionine over a long period of time in case of hydrolyzing 5-(β-methylmercaptoethyl)hydantoin in the presence of potassium carbonate, the process enabling excellent corrosion resistance of an equipment.

2. Description of the Related Art

A process for hydrolyzing 5-(β-methylmercaptoethyl)hydantoin (hereinafter referred to as M-hydantoin) to obtain methionine is usually carried out in such a manner as shown in the following scheme in the presence of an alkali.

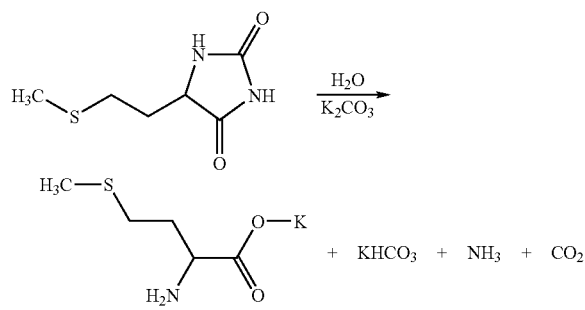

This hydrolysis reaction is usually carried out under the condition of a pressure of about 0.5 to 1.5 MPaG and a temperature of about 150 to 200° C. When potassium carbonate is used as the alkali, a metallic material is extremely likely to be corroded under the hydrolysis condition regardless of a liquid phase or a vapor phase. A SUS 304L stainless steel is corroded and a high-grade austenitic chromium-nickel stainless steel, which is said to be more excellent in corrosion resistance, is also insufficient in corrosion resistance to such an environment.

Under such an environment, zirconium, which forms a stable zirconium oxide film on the surface, shows excellent corrosion resistance, but has such a problem that it is expensive and is inferior in workability.

Under these circumstances, it is known that a stainless steel containing 21.0 to 30.0% by weight of a Cr element, 4.5 to 11.0% by weight of a Ni element, 2.5 to 5.0% by weight of a Mo element and 0.05 to 0.35% by weight of a N element as chemical components in metal has excellent corrosion resistance for an equipment material in such an environment (Japanese Unexamined Patent Publication (Kokai) No. 11-217370).

SUMMARY OF THE INVENTION

While hydrolysis at higher temperature is required so as to increase a hydrolysis rate, higher corrosion resistance is required to a metallic material used in an equipment under the condition at higher temperature and also an equipment material having excellent corrosion resistance even under the condition at higher temperature is required.

An object of the present invention is to provide a process for stably producing methionine over a long period of time in case of hydrolyzing 5-(β-methylmercaptoethyl)hydantoin in the presence of potassium carbonate, the process enabling an equipment to resist corrosion quite well.

The present invention provides a process for producing methionine, which comprises using, as an equipment material for a step of hydrolyzing 5-(β-methylmercaptoethyl)hydantoin in the presence of potassium carbonate to produce methionine, a stainless steel containing 21.0 to 30.0% by weight of a Cr element, 2.5 to 11.0% by weight of a Ni element and 1.0 to 5.0% by weight of a Mo element, a ratio of the total content of the Cr element and the Mo element to the content of the Ni element being from 4.7 to 14.0.

According to the process of the present invention, even if M-hydantoin is hydrolyzed at high temperature in the presence of potassium carbonate, methionine can be stably produced over a long period of time, the process enables an equipment to resist corrosion quite well, and thus its industrial utility value is great.

DETAILED DESCRIPTION OF THE INVENTION

The reaction for producing methionine in the present invention is a reaction in which M-hydantoin is hydrolyzed in the presence of potassium carbonate to produce methionine, and methionine is usually obtained in the form of a potassium salt by hydrolysis. The hydrolysis is usually carried out under the condition of a pressure of about 0.5 to 1.5 MPaG and a temperature of about 150 to 200° C. for about 10 to 120 minutes. Ammonia and a carbon dioxide gas generated during hydrolysis are recovered and are preferably utilized in the step of obtaining M-hydantoin.

Then, the solution obtained by the hydrolysis is usually neutralized with a carbon dioxide gas to precipitate methionine. Usually, precipitation through neutralization is carried out while pressurizing with a carbon dioxide gas and the precipitated methionine is filtered, separated, optionally washed with water and then dried to obtain methionine as a product.

In the present invention, in case of producing methionine by such a reaction, a stainless steel containing 21.0 to 30.0% by weight of a Cr element, 2.5 to 11.0% by weight of a Ni element and 1.0 to 5.0% by weight of a Mo element, a ratio of the total content of the Cr element and the Mo element to the content of the Ni element being from 4.7 to 14.0, preferably a stainless steel containing 21.0 to 30.0% by weight of a Cr element, 4.5 to 11.0% by weight of a Ni element and 2.5 to 5.0% by weight of a Mo element, a ratio of the total content of the Cr element and the Mo element to the content of the Ni element being from 4.7 to 8.2, is used as an equipment material.

The use of the stainless steel as the equipment material includes that the equipment is composed of the stainless steel or the equipment is lined, and also a valve, a piping and the like attached to the equipment are configured.

In the present invention, the equipment material is preferably used at least in an equipment used in the above hydrolysis step.

In the stainless steel, when the content of the Cr element is too small, excellent corrosion resistance to the hydrolysis reaction cannot be maintained. On the other hand, when the content of the Cr element is too large, the resulting stainless steel shows severe brittleness. It is known that the presence of the Ni element deteriorates corrosion resistance of the stainless steel in the hydrolysis reaction system. When the content of the Ni element is within the above range, corrosion resistance does not substantially deteriorate and the Ni element exerts the effect of improving mechanical properties and workability, to the contrary. When the content of the Mo element is within the above range, it exerts excellent corrosion resistance to the hydrolysis. When the content of the Mo element is too large, workability deteriorates and thus sigma brittleness may be accelerated.

In the stainless steel used in the present invention, the contents of the Cr element, the Ni element and the Mo element are within the above range and also a ratio of the total content of the Cr element and the Mo element to the content of the Ni element is from 4.7 to 14.0.

When the ratio is too small, corrosion resistance is not improved. On the other hand, when the ratio is too large, it is not preferred because the content of the Cr element becomes too large and thus brittleness becomes severe.

The stainless steel used in the present invention, for example, includes a portion among SUS329J4L and UNS S32906. All of SUS329J4L and UNS S32906 cannot be used and those satisfying the above composition are selected and used.

|        | SUS304L    | SUS329J4L  | UNS S32906 |
|--------|------------|------------|------------|
| C      | ≦0.030     | ≦0.030     | ≦0.030     |
| Si     | ≦1.00      | ≦1.00      | ≦0.50      |
| Mn     | ≦2.00      | ≦1.50      | 0.80-1.50  |
| P      | ≦0.045     | ≦0.040     | ≦0.030     |
| S      | ≦0.030     | ≦0.030     | ≦0.030     |
| Ni     | 9.00-13.00 | 5.50-7.50  | 5.8-7.5    |
| Cr     | 18.00-20.00| 24.00-26.00| 28.0-30.0  |
| Mo     | —          | 2.50-3.50  | 1.50-2.60  |
| Cu     | —          | —          | ≦0.80      |
| N      | —          | 0.08-0.30  | 0.30-0.40  |
| Others | —          | —          | —          |

The stainless steel used in the present invention preferably contains 0.05 to 0.40% by weight of the N element. When the content of the N element is within the above range, the effect of improving corrosion resistance is exerted with the increase of the content of the N element. When the content of the N element is too large, nitrides are precipitated in an alloy and thus toughness may deteriorate.

The stainless steel used in the present invention may contain a W element and/or a Cu element. In this case, the content of the W element is usually about 2.50% by weight or less, and preferably from about 0.10 to 2.50% by weight. The content of the Cu element is usually about 0.80% by weight or less, and preferably from about 0.20 to 0.80% by weight. The W element is a component element which is effective to improve corrosion resistance while suppressing embrittlement of the stainless steel due to precipitation of a sigma phase. On the other hand, the Cu element is a component element which is effective to improve general corrosion resistance of the stainless steel.

EXAMPLES

The process of the present invention will now be described in more detail by way of the following Examples, which are for illustrative purpose only and by no means limit the process of the present invention.

In the Examples, each content of chemical components of a stainless steel is measured by a fluorescent X-ray spectrometer.

Example 1

In a piping (pressure: 0.5 to 1.5 MPaG, temperature: 170 to 190° C.) in which an aqueous hydrolysis feed solution prepared by mixing 5-(β-methylmercaptoethyl)hydantoin with potassium carbonate (concentration of hydantoin: about 9% by weight, concentration of potassium carbonate: about 10% by weight) is circulated, specimens shown in Table 1 were placed and a corrosion test was carried out by allowing the specimens to stand for 8,760 hours. Almost all of balance of chemical components is composed of Fe.

With respect to the results of the corrosion test, a corrosion rate (reduction in thickness per year) was obtained by calculating from the measured corrosion degree (decrease in weight of a specimen per unit time per unit area). The results are shown in Table 1.

TABLE 1

|  |  | Chemical components (% by weight) | | | | | | Corrosion rate |
|---|---|---|---|---|---|---|---|---|
|  | Alloy | Cr | Ni | Mo | N | W | (Cr + Mo)/Ni | (mm/year) |
| Examples | Alloy A | 25.05 | 5.62 | 3.21 | 0.20 | 0.0 | 5.03 | 0.09 |
|  | Alloy B | 28.53 | 6.38 | 2.53 | 0.35 | — | 4.87 | 0.02 |
| Comparative | Alloy C | 25.34 | 6.87 | 3.45 | 0.17 | — | 4.19 | 0.27 |
| Examples | Alloy D | 24.73 | 6.67 | 3.32 | 0.16 | 0.0 | 4.21 | 0.32 |

While an alloy C and an alloy D, which showed excellent corrosion resistance at 170° C., do not show sufficient corrosion resistance under the condition of a temperature of higher than 170° C., an alloy A and an alloy B according to the present invention show excellent corrosion resistance even under this condition.

The present application has been filed claiming the Paris Convention priority based on Japanese Patent Application No. 2006-120176 (filed on Apr. 25, 2006, entitled "Process for Producing Methionine") and Japanese Patent Application No. 2006-333069 (filed on Dec. 11, 2006, entitled "Process for Producing Methionine"). The contents of those applications are incorporated herein by reference thereto in their entirety.

The invention claimed is:

1. A process for producing methionine, which comprises using, as an equipment material for a step of hydrolyzing 5-(β-methylmercaptoethyl)hydantoin in the presence of potassium carbonate to produce methionine, a stainless steel containing 21.0 to 30.0% by weight of a Cr element, 2.5 to 11.0% by weight of a Ni element and 1.0 to 5.0% by weight of a Mo element, a ratio of the total content of the Cr element and the Mo element to the content of the Ni element being from 4.7 to 14.0.

2. The process for producing methionine according to claim 1, which comprises using, as the equipment material, a stainless steel containing 21.0 to 30.0% by weight of a Cr element, 4.5 to 11.0% by weight ofaNi element and 2.5 to 5.0% by weight of a Mo element, a ratio of the total content of the Cr element and the Mo element to the content of the Ni element being from 4.7 to 8.2.

3. The process for producing methionine according to claim 1, which comprises using, as the equipment material, a stainless steel further containing from about 0.10 to 2.50% by weight of a W element.

4. The process for producing methionine according to claim 2, which comprises using, as the equipment material, a stainless steel further containing from about 0.10 to 2.50% by weight of a W element.

5. The process for producing methionine according to claim 1, which comprises using, as the equipment material, a stainless steel further containing from about 0.20 to 0.80% by weight of a Cu element.

6. The process for producing methionine according to claim 2, which comprises using, as the equipment material, a stainless steel further containing from about 0.20 to 0.80% by weight of a Cu element.

7. The process for producing methionine according to claim 1, which comprises using, as the equipment material, a stainless steel further containing from about 0.10 to 2.50% by weight of a W element and from about 0.20 to 0.80% by weight of a Cu element.

8. The process for producing methionine according to claim 2, which comprises using, as the equipment material, a stainless steel further containing from about 0.10 to 2.50% by weight of a W element and from about 0.20 to 0.80% by weight of a Cu element.

* * * * *